United States Patent [19]

Berglund et al.

[11] Patent Number: 5,034,105
[45] Date of Patent: Jul. 23, 1991

[54] CARBOXYLIC ACID PURIFICATION AND CRYSTALLIZATION PROCESS

[75] Inventors: Kris A. Berglund, Okemos; Ponnampalam Elankovan, Grand Rapids; David A. Glassner, Okemos, all of Mich.

[73] Assignee: Michigan Biotechnology Institute, East Lansing, Mich.

[21] Appl. No.: 385,638

[22] Filed: Jul. 27, 1989

[51] Int. Cl.⁵ .............................................. B01D 9/02
[52] U.S. Cl. .............................. 204/182.4; 204/182.6; 562/593; 562/607; 562/608; 562/580; 435/136; 435/140
[58] Field of Search .................. 204/182.4, 182.6, 301; 435/136, 140; 562/593, 607, 608, 580

[56] References Cited

U.S. PATENT DOCUMENTS

| | | | |
|---|---|---|---|
| 4,100,188 | 7/1978 | Kao | 562/580 |
| 4,110,175 | 8/1978 | Ahlgren et al. | 204/180 P |
| 4,137,260 | 1/1979 | Walter | 562/580 |
| 4,146,730 | 3/1979 | Nishikido et al. | 562/593 |
| 4,678,553 | 7/1987 | Mandle et al. | 204/182.6 |
| 4,766,161 | 8/1988 | Chlanda et al. | 521/27 |
| 4,781,809 | 11/1988 | Falcone, Jr. | 204/182.4 |
| 4,874,700 | 10/1989 | Seipenbusch | 562/593 |

FOREIGN PATENT DOCUMENTS 8318631 5/1985 France .

OTHER PUBLICATIONS

Hongo, M., Nomura. Y. and M. Iwahara, "Novel Method of Lactic Acid Production by Electrodialysis Fermentation," Appl. Environ, Microbiol. 52, 2, 314-319, Aug. 1986.

Nomura, Y., Iwahara, M. and M. Hongo, "Lactic Acid Production by Electrodialysis Fermentation Using Immobilized Growing Cells." Biotechnol. & Bioeng. 30, 788-793, Oct. 1987.

Caspari et al., Arch Microbiol., vol. 135, pp. 16-24 (1983).

Davis et al., Int. J. Syst. Bacteriol., vol. 26, pp. 498-504 (1976).

"AQUATECH" System, product brochure, Allied Signal Corporation, 1985.

Hopgood et al., Aust. J. Biol. Sci., vol. 20, pp. 165-192 (1967).

Caldwell et al., J. Bacteriol., vol. 98, pp. 668-676 (1969).

Primary Examiner—John F. Niebling
Assistant Examiner—Arun S. Phasge
Attorney, Agent, or Firm—Quarles & Brady

[57] ABSTRACT

A process for preparing a carboxylic acid of high purity comprises preparing an undersaturated solution of a salt of the carboxylic acid; subjecting the undersaturated salt solution to water-splitting electrodialysis to form base and a supersaturated solution of the carboxylic acid; and, then crystallizing the carboxylic acid from the supersaturated solution. In the preferred embodiment, the undersaturated solution is a fermentation broth containing sodium succinate and the carboxylic acid obtained is succinic acid.

7 Claims, 1 Drawing Sheet

CARBOXYLIC ACID PURIFICATION AND CRYSTALLIZATION PROCESS

RELATED CASES

This application is a continuation-in-part of earlier copending application U.S. patent Ser. No. 07/325,404 filed Mar. 17, 1989.

FIELD OF THE INVENTION

This invention generally relates to an improved process for the purification and crystallization of carboxylic acids. More particularly, it relates to a novel process in which an aqueous solution of sodium succinate is converted to a supersaturated solution of succinic acid from which high purity succinic acid is crystallized.

Background of the Invention

Succinic acid and its derivatives are widely used as specialty chemicals with applications in polymers, foods, pharmaceuticals, and cosmetics. Furthermore, succinic acid is a valuable 4-carbon intermediate useful in processes for the production of 1,4-butanediol, tetrahydrofuran, and gamma-butyrolactone. These processes require material of high purity since the end products are produced by chemical catalysts which can be poisoned by impurities.

For a fermentation based carboxylic acid process to be economically attractive for the production of specialty and commodity chemicals, the development of a low-cost fermentation must be combined with low cost and efficient product recovery and purification methods. The anaerobic fermentations which are most promising for the production of organic acids usually operate optimally at pH's where salts of the organic acids rather than the free acids are formed. However, the free acids and their derivatives are the articles of commercial interest. In addition, contaminating proteins and cell by-products need to be removed from the free carboxylic acids because of their interference in chemical catalysis. Therefore, an effective fermentation and recovery process must remove both cells and proteins and subsequently convert the acid salts to free acids of high purity.

Several possible alternatives exist for the preliminary recovery of succinic acid salts from the fermentation broth. For example, we have previously demonstrated that the use of conventional electrodialysis with special membranes can be employed to recover succinates from whole fermentation broths and that the succinate can be converted into the free succinic acid by water-splitting electrodialysis using the high efficiency bipolar membranes described in Chlanda et al. U.S. Pat. No. 4,766,161.

BRIEF SUMMARY OF THE INVENTION

It is a general object of the present invention to disclose a novel method of obtaining a carboxylic acid of high purity by using water-splitting electrodialysis to convert an undersaturated aqueous solution of a carboxylic acid salt into a supersaturated aqueous solution of the free acid and then crystallizing the acid from the solution.

In the inventive process of the present invention, an undersaturated carboxylic acid salt aqueous solution is subjected to water-splitting electrodialysis to form a supersaturated solution of the free carboxylic acid. Free carboxylic acid of high purity is then crystallized from the supersaturated solution by conventional means, such as seeding with acid crystals.

The present invention is especially useful with succinic acid because sodium succinate is considerably more water soluble than free succinic acid. In addition, we have unexpectedly discovered that the water-splitting electrodialysis converts sodium acetate which inhibits the crystallization of succinic acid into free acetic acid which promotes such crystallization.

DESCRIPTION OF PREFERRED EMBODIMENT

In the preferred embodiment of the present invention, the feed stream is a fermentation broth obtained by an anaerobic fermentation of a low cost carbohydrate substrate by *Anaerobiospirillum succiniciproducens* in the presence of sodium ions and added tryptophan. The broth is an aqueous preparation which contains both sodium succinate and sodium acetate.

Figure 1:
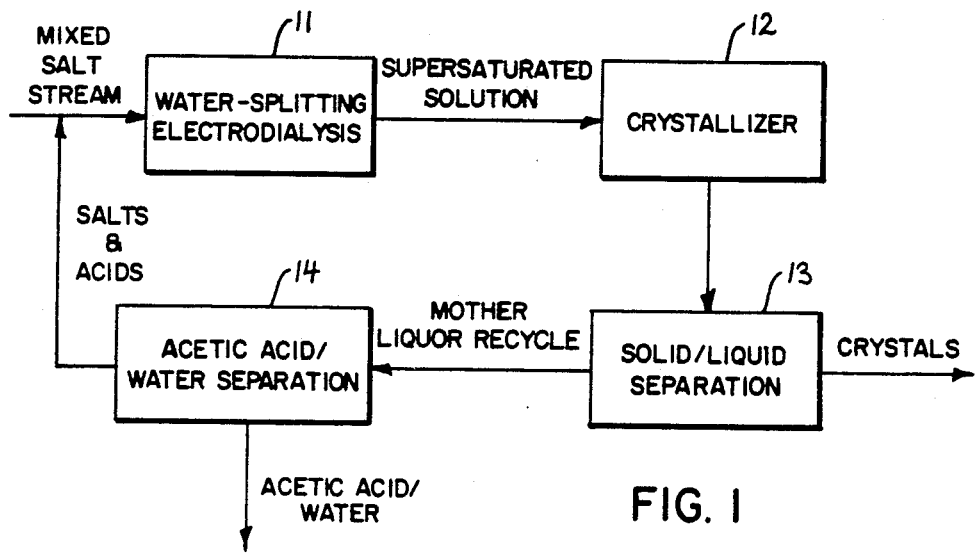
FIG. 1 is a schematic flow diagram of the process of the present invention.

A schematic diagram of the process of the present invention is shown in FIG. 1. A mixed salt stream containing both sodium acetate and sodium succinate is concentrated to about 10 to about 25% succinate by weight prior to introduction into the water-splitting electrodialysis unit 11. While in the preferred embodiment conventional electrodialysis is used to perform this task, other unit operations may also be feasible. The mixed salt stream which is undersaturated with sodium succinate is then treated using water-splitting electrodialysis. The resulting stream from the water-splitting electrodialysis unit contains some residual sodium salts and free succinic and acetic acids; it is supersaturated with respect to succinic acid. This solution is then seeded with crystals of succinic acid in a crystallizer 12 or other suitable vessel. The succinic acid slurry from the crystallizer is then taken to a solid/liquid separator 13, e.g. a hydrocyclone or microfiltration unit, to separate the crystals which are then available as product or for re-use as seeds.

The liquid from the separator 13 can be treated in a suitable vessel 14 to remove some of the water and the acetic acid and then recycled to the feed stream. This may be accomplished by a number of different operations. The appropriate use of acetic acid removal will allow optimization of acetic acid concentration for crystallization to be obtained.

Figure 2:
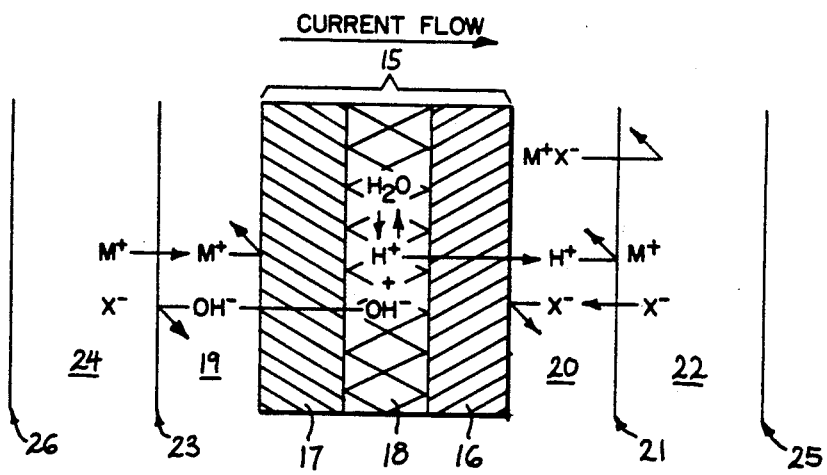
FIG. 2 is a schematic illustration of the water-splitting electrodialysis of a salt solution to generate a free acid and a base.

The fundamental concept by which water-splitting electrodialysis may be used to produce succinic acid and a base sodium hydroxide can be understood by reference to FIG. 2 in which a greatly magnified portion of a bipolar membrane 15, not drawn to scale, is shown schematically. The bipolar membrane consists of three portions, a cation selective portion, 16, an anion selective portion, 17, and an interface region, 18, between the anion and cation portions. When a direct current is passed across the bipolar membrane as shown, the transport of ions between solutions 19 and 20 is interrupted since anions are excluded from the cation side 16 and cations are excluded from the anion side 17. Since little or no salt is present in the interface region 18, the dissociation of water to $H^+$ and $OH^-$ provides the ions for carrying the current across the membrane. Water at the interface is replaced by diffusion through the anion, portion 17, and cation portion 16, from the solutions 19 and 20, respectively. When used in conjunction with monopolar membranes (one arrangement of which is shown in FIG. 2) the bipolar membrane functions to produce the ions needed to generate succinic acid and base from sodium succinate (MX). If membrane 21 is an anion permeable membrane, then as $H^+$ enters solution 20 from the bipolar membrane, 15, an equivalent amount of $X^-$ will enter solution 20 from compartment 22 producing a solution of succinic acid (HX) in solution 20. Similarly, if membrane 23 is a cation membrane, then as $OH^-$ enters solution 19 from the bipolar membrane 15, $M^+$ will enter solution 19 from compartment 24 to form a solution of sodium hydroxide (MOH).

In the current application both membranes 21 and 23 are cation exchange membranes. This configuration creates compartments 20 and 24 which contain both the free acid (e.g. succinic acid) and the salt from which it came (e.g. sodium succinate). In order to regenerate base, membranes 25 and 26 will be bipolar membranes. The base streams will then be 19 and 22.

The electrical potential required to generate acid and base by means of a bipolar membrane, as given by electrochemical theory, should be on the order of 0.8 volts to produce 1N solutions of strong acid and base. Some additional potential is also required to overcome the resistance to transport of $H^+$ and $OH^-$ through the cation and anion portion of the membrane, respectively. The production of bipolar membranes exhibiting a potential drop of less than 1.2 volts in 0.5M $Na_2SO_4$ at about 30° C. and at high current densities (e.g. 100 $A/ft^2$)($10^9$ $mA/cm^2$) has been reported in the Chlanda et al. U.S. Pat. No. 4,766,161, which is incorporated by reference herein.

The invention is further illustrated by reference to the examples.

EXAMPLES

General Procedures

Preparation of Succinate Salt

Succinate salt solutions are prepared by anaerobic fermentations using a strain of *Anaerobiospirillum succinici producens* (deposited in the American Type Culture Collection as ATCC 29305 and redeposited under the provision of the Budapest Treaty as ATCC 53488) at 39° C. in a fermentor with an initial volume of 55l for 29 hours. The fermentor used is an 80l New Brunswick Scientific Pilot Plant Fermentor. The media contains approximately 35 g/l dextrose, 10 g/l corn steep liquor, and 25 ppm tryptophan. A 5% inoculum is used. The pH is maintained between 6.1-6.3 by addition of sodium carbonate on a demand basis. Agitation speed is 100 rpm.

The cells in the fermentation broth may be removed by processing the broth through an AMICON DC-30 ultrafiltration unit with a hollow fiber cartridge of 0.2 l micron pore size.

Concentration of the Succinate Solution

The sodium succinate concentration in the broth can be
adjusted to the desired concentration of about 10% to about 25% by weight by using a conventional electrodialysis unit. The electrodialysis stack consists of an alternating series of anion and cation selective membranes separated by flow distribution gaskets. The membranes are bound on one end by an anolyte compartment and an anode while on the other end by a catholyte compartment and cathode. The preferred stack pack for evaluation is available from HPD Inc. (Naperville, IL) and contains membranes manufactured by Asahi Glass Co. (Japan). The stack pack may contain the following:
  10 cell pairs
  anion membrane—AMV
  cation membrane—CMR
  effective area—178 $cm^2$
  electrolyte—1M Sodium Succinate in Water The unit consists of three independent flow channels fed to the electrodialyzer stack pack. The three streams are:
  (1) diluting stream—feed materials, broth
  (2) concentrating stream—product
  (3) electrolyte—sodium succinate From each reservoir, material is pumped through a valve, rotameter, pressure gauge, the stack pack, and then back to the reservoir.

The electrical current is supplied by a Hewlett Packard (HP) regulated DC power supply model 6268B. It is connected to the anode and cathode of the membrane stack and can produce 0-20 amperes and deliver 0-50 volts. A Fluke A75 multimeter is used to measure the voltage drop across selected cell pairs. Two platinum wires are inserted between eight cell pairs and then connected to the voltmeter.

Conversion of Succinate to Succinic Acid

A suitably concentrated but undersaturated succinate solution obtained by conventional electrodialysis and sometimes evaporation also can be converted into a supersaturated succinic acid solution by passing it through a water-splitting electrodialysis unit 10.

The preferred unit contains Aquatech (Warren, N.J.) bipolar membranes and is a two compartment stack. The stack which is schematically illustrated in FIG. 1 consists of alternating cation permeable and bipolar membranes. The anode and cathode compartments are bound by a Nafion membrane at each end of the membrane stack.

The test membrane stack contains the following:
  8 cell pairs
  -cation membrane
  -bipolar membrane
  effective area 102. 4 $cm^2$
  electrolyte (2.5N NaOH)

The unit consists of three independent flow channels fed to the electrodialyzer stack. The three streams are:
  1. Acid stream (initially the sodium succinate salt stream)
  2. Base stream (becomes more concentrated as run proceeds)
  3. Electrode rinse stream (2.5N NaOH)

Conductivity was measured using a portable conductivity meter (Cole Parmer model 1484-10).

Succinate and acetate concentrations are the anion concentration and were measured after appropriate dilution and acidification by an HPLC method using a 1 ft long HP×87 $H^+$ column of BioRad (Calif., U.S.A.).

Total protein content was determined by Kjeldahl apparatus and reported as nitrogen ×6.25%.

Sulfate concentration was determined by gravimetric determination of barium sulfate precipitation. Sodium concentration was determined using an Orion SA 720 ion selective meter and a sodium electrode.

Crystallization of Succinic Acid from Supersaturated Solution

The crystallization of succinic acid of high purity from the supersaturated solution is conducted at 30° C. using 125 ml of broth obtained after water-splitting electrodialysis. The supersaturated solution is seeded with crystals of pure succinic acid in a crystallizer. The crystals of succinic acid which formed are filtered and washed with cold water. The resulting crystals when analyzed for succinate, acetate, protein, sodium, and sulfate are found to be of high purity (about 99.9%).

EXAMPLE 1

Effect of Impurities on Crystallization

TABLE 1

PROCESS STREAM COMPOSITIONS (WEIGHT % COMPOSITION, DRY BASIS)

|  | Fermentor Product | After ED | Water-Splitting ED | After Crystallization |
|---|---|---|---|---|
| Succinate | 51.5 | 63.0 | 77.6 | 99.91 |
| Acetate | 13.2 | 8.8 | 18.6 | — |
| Protein | 9.7 | 0.8 | 0.6 | 0.07 |
| Sodium | 25.6 | 27.3 | 2.8 | 0.02 |
| Sulfate | 0.1 | 0.6 | 0.4 | — |

Table 1 shows the process stream compositions obtained after each step in the process. The main items to note are the relative compositions of the solution after water-splitting and the composition of the crystalline material obtained from it. The extreme purity of the crystalline material indicates that crystallization is a viable means for product purification.

The concentrations from the fermentor, after conventional electrodialysis, and prior to the water-splitting electrodialysis were 50.2, 146.7, and 215.9 gm dissolved solids/liter, respectively. Clearly, the stream leaving the conventional electrodialysis was further concentrated by evaporation prior to water-splitting. This step is necessary only to the extent to create a supersaturated solution after water-splitting.

EXAMPLES 2 AND 3

A separate set of crystallization experiments was performed to determine the effect of acetic acid/sodium acetate on succinic acid crystallization. Compositions were chosen to mimic those found after water-splitting: 1.5M succinic acid; 0.5M sodium acetate; and either 0.2M sodium acetate or acetic acid.

TABLE 2

THE EFFECT OF ACETIC ACID AND SODIUM ACETATE ON SUCCINIC ACID CRYSTALLIZATION AT 30° C. FOR A MODEL SYSTEM DESIGNED TO MIMIC BROTH CONDITIONS

|  | Ex. 2 | Ex. 3 |
|---|---|---|
| Water, gm | 180 | 180 |
| Sodium succinate, gm | 16.2 | 16.2 |
| Succinic acid, gm | 35.4 | 35.4 |
| Sodium acetate, gm | 6.8 | — |
| Acetic acid, gm | — | 3.2 |
| Crystal yield, gms | 1.22 | 5.17 |

The results of the acetic acid/sodium acetate impurity studies in Table 2 show four times more succinic acid crystals formed in the presence of acetic acid than sodium acetate. These results indicate acetic acid has a crystal

EXAMPLES 4, 5 AND 6

In a companion study, sodium acetate and acetic acid are added to broth solutions which are supersaturated. As demonstrated by Table 3, addition of acetic acid greatly enhances yield while sodium acetate causes a complete cessation of crystallization.

TABLE 3

THE EFFECT OF ADDED ACETIC ACID AND SODIUM ACETATE ON SUCCINIC ACID CRYSTALLIZATION AT 30° C. FOR THE FERMENTATION PRODUCT

| Experiment Number | Ex. 4 | Ex. 5 | Ex. 6 |
|---|---|---|---|
| Broth, ml | 200 | 200 | 200 |
| Sodium Acetate, gm | 6.8 | — | — |
| Acetic acid, gm | — | 3.2 | — |
| Crystal yield, gm/l | — | 18.0 | 11.5 |

EXAMPLE 7 AND 8

The ability to remove high quality crystals from solution produced by water-splitting has several implications. Clearly, creation of supersaturation by water-splitting is demonstrated. This phenomenon should occur in any system wherein the salt is more soluble than the acid. As can be seen in Table 4 this can be accomplished without the formation of crystals on the membrane and current efficiency is preserved during the process. Finally, the crystallization step is not only feasible for removing impurities but facilitated by their presence.

TABLE 4

WATER-SPLITTING ELECTRODIALYSIS RECOVERY OF SUCCINIC ACID FROM FERMENTATION PRODUCT

|  | Ex. 7 | Ex. 8 |
|---|---|---|
| Sodium Removal, % | 78.9 | 81.2 |
| Salt Stream |  |  |
| Initial Succinate Conc., g/l | 78 | 126 |
| Final Succinate Conc., g/l | 91 | 52 |
| Initial Acetate Conc., g/l | 13 | 29 |
| Final Acetate Conc., g/l | 15 | 36 |
| Temperature, °C. | 45 | 45 |
| Current Efficiency, % | 78.9 | 76.2 |
| Crystallization* | No | Yes |
| Membrane Fouling | No | No |

*Supersaturated with respect to succinic acid.

The recovery per pass using water-splitting electrodialysis was low with only 21.8 gm/l of crystals produced. For this reason the process should be thought of as a "stripping" crystallization, wherein the succinic acid in excess of solubility is "stripped" from solution by crystallization.

It will be apparent to those skilled in the art that the relationship of impurities to crystallization is quite complex. In the preferred embodiment of the process of the present invention impurities, such as amino acids and salts, are effectively excluded from the succinic acid crystals. In addition, we have discovered that the crystallization of succinic acid is unexpectedly inhibited by the presence of sodium acetate while it is enhanced by the presence of acetic acid. This remarkable result shows that the use of water-splitting electrodialysis not only creates solutions supersaturated with respect to succinic acid, but also converts a crystallization inhibiter, sodium acetate, to a crystallization promoter, acetic acid.

It also will be apparent that the foregoing description has been for purposes of illustration and that the process can be used to prepare other free carboxylic acids, such as maleic, fumaric, citric or amino acids such as glutamic acid.

Representative of the carboxylic acid salts which can be used in the process of the present invention are those having salts that are more water soluble than the free acids. Those salts are usually the sodium, potassium and ammonium salts but may be other salts in some cases.

From the foregoing, it will be apparent to those skilled in the art, that water-splitting electrodialysis can be used to produce supersaturated carboxylic acid solutions from undersaturated acid salt solutions; that nucleation of crystals on the membrane surface is not important; and that a highly purified crystalline acid product can be obtained from a fermentation broth. Other advantages of the process will be apparent to those skilled in the art. Therefore, it is intended that the invention be limited only by the claims.

REFERENCES

1. Chlanda, F. P. and M. J. Lan. 1988. U.S. Pat. No. 4,766,161 (Allied Corp.).
2. DeThomas, W. and E. V. Hatt. 1978. U.S. Pat. No. 4,105,674 (GAF Corp.).
3. Glassner, D. A. and R. Datta. 1989. MBI Internal Report.
4. Kitson, M. and P. S. Williams. 1988. U.S. Pat. No. 4,777,303 (BP Chemicals Ltd.).
5. Mani, K. N. and W. L. Johnson. 1988. 1988 Sixth Annual Membrane Technology/Planning Conference, Nov. 1-3, 1988, Cambridge, Ma.
6. Marshall, H. and D. Bain. 1910. J. Chem. Soc. Trans. 47:1074.

We claim:

1. An improved method of crystallizing succinic acid from a supersaturated solution of succinic acid which comprises adding to said solution an effective amount of acetic acid to enhance the crystallization of the succinic acid.

2. A process for the production and purification of succinic acid which comprises:
   (a) anaerobically growing a succinate producing microorganism on a carbohydrate substrate to produce a broth containing a succinate salt and an acetate salt;
   (b) subjecting the broth to conventional electrodialysis to prepare an aqueous concentrated but unsaturated succinate solution which also contains acetate;
   (c) subjecting the unsaturated succinate solution containing acetate to water splitting electrodialysis to produce a supersaturated succinic acid solution; and
   (d) then crystallizing the succinic acid from the supersaturated solution.

3. A process for the production and purification of succinic acid which comprises:
   (a) anerobically growing a succinate producing microorganism on a carbohydrate substrate to produce a broth containing acetate and succinate;
   (b) concentrating the broth containing acetate and succinate salts;
   (c) subjecting the concentrated broth to water splitting electrodialysis which converts the succinate in the broth to succinic acid and the acetate in the broth to acetic acid which promotes the crystallization of succinic acid; and
   (d) then crystallizing the succinic acid from the supersaturated succinic acid solution.

4. A process of claim 3 in which the broth is concentrated and purified in step (b) by subjecting it to conventional electrodialysis.

5. A process of claim 3 in which the aqueous preparation from which the succinic acid has been crystallized is concentrated and recycled to step (a).

6. A process of claim 3 in which the succinic acid in step (c) is crystallized by seeding the supersaturated solution with crystals of succinic acid.

7. An improved method of crystallizing succinic acid from a supersaturated solution of succinic acid which comprises conducting the crystallization in the presence of an effective amount of acetic acid to enhance the crystallization of the succinic acid.

* * * * *